United States Patent [19]

Hirama et al.

[11] 4,427,940
[45] Jan. 24, 1984

[54] ELECTROMAGNETIC INSPECTING APPARATUS FOR MAGNETIZABLE WIRE ROPE

[75] Inventors: Yutaka Hirama, Ibaraki; Kenzoh Takahashi, Musashino; Sadayuki Hori, Tokyo, all of Japan

[73] Assignee: Hitachi Elevator Engineering and Service Co., Ltd., Tokyo, Japan

[21] Appl. No.: 256,107

[22] Filed: Apr. 21, 1981

[30] Foreign Application Priority Data

Apr. 21, 1980 [JP] Japan .................................. 55-51661

[51] Int. Cl.³ ...................... G01N 27/82; G01R 33/12
[52] U.S. Cl. .................................... 324/240; 324/243; 324/206
[58] Field of Search ............... 324/207, 239, 240, 241, 324/242, 243, 206; 336/30, 214, 233

[56] References Cited

U.S. PATENT DOCUMENTS 1,322,405 11/1919 Burrows ............................. 324/240
4,270,088 5/1981 Weischedel ........................ 324/242

FOREIGN PATENT DOCUMENTS 55-114747 4/1980 Japan .................................. 324/240

Primary Examiner—Gerard R. Strecker
Assistant Examiner—Walter E. Snow
Attorney, Agent, or Firm—Antonelli, Terry & Wands

[57] ABSTRACT

An electromagnetic inspecting apparatus for electromagnetically detecting a defect present in a magnetizable wire rope moving in its longitudinal direction is disclosed. The apparatus comprises a first magnetic pole disposed opposite to the elongate magnetic member, a second magnetic pole having a polarity different from that of the first magnetic pole and disposed opposite to the elongate magnetic member at a position spaced apart by a predetermined distance from the first magnetic pole in the longitudinal direction, a detecting core disposed opposite to the magnetizable wire rope at a position intermediate between the first and second magnetic poles, a detecting coil wound around the detecting core to make a differential response to flows of leakage flux appearing due to the presence of a defect in the magnetizable wire rope thereby generating an electrical output signal indicative of the result of its response, and a yoke magnetically coupling the first and second magnetic poles and the detecting core at the portions remote from the elongate magnetic member.

42 Claims, 13 Drawing Figures

ELECTROMAGNETIC INSPECTING APPARATUS FOR MAGNETIZABLE WIRE ROPE

BACKGROUND OF THE INVENTION

1. Field of the Invention

This invention relates to an electromagnetic inspecting apparatus which is suitable for electromagnetically detecting a defect present in a magnetizable wire rope used, for example, for the traction of an elevator cage in an elevator system or a cable car in a cable railway.

2. Description of the Prior Art

In a wire rope used generally for the traction of an elevator cage in an elevator system or a cable car in a cable railway, one or more of wires constituting the wire rope may be broken or locally worn during a long period of time of use, resulting in a gradual reduction of the residual mechanical strength of the wire rope. It is therefore a common practice to periodically inspect the wire rope for the presence of such a defect so as to replace the wire rope by a new one before a serious accident occurs.

While visual inspection was mostly resorted to in the past for the inspection of the presence or absence of a defect in such a rope, a method of magnetically inspecting such a rope for the presence or absence of a defect has recently been put into practice although such a manner of inspection has not yet been widely employed in this field. A known publication, for example, Japanese Utility Model Publication No. 2047/'75 discloses a detector for use in an electromagnetic inspecting apparatus for detecting a defect present in a steel wire rope. According to the disclosure of this known publication, a steel wire rope previously magnetized by an exciter or magnetizer is passed through the detector comprising a detecting coil which detects the intensity of leakage magnetic flux appearing when a defect is present in the steel wire rope. However, due to the fact that such a manner of inspection can detect merely the intensity of leakage flux, the proposed method has been defective in that the sensitivity of defect detection is considerably low, and there is also a great tendency of mixing of noise into the detector output signal, resulting in difficulty of ensuring the desired sufficient accuracy of defect detection.

SUMMARY OF THE INVENTION

It is therefore a primary object of the present invention to provide an electromagnetic inspecting apparatus which obviates the prior art defect pointed out above and ensures the desired high accuracy of defect detection.

An embodiment of the electromagnetic inspecting apparatus according to the present invention which attains the above object comprises a spaced pair of a first and a second magnetic pole each disposed opposite to an elongate member of magnetic material moving in its longitudinal direction, a detecting core having a detecting coil wound therearound and disposed opposite to the elongate magnetic member at a position intermediate the first and second magnetic poles, and a common yoke magnetically coupling the first and second magnetic poles and the detecting core at the portions remote from the elongate magnetic member, the second magnetic pole having a polarity different from that of the first magnetic pole.

DESCRIPTION OF THE PREFERRED EMBODIMENTS

Figure 1:
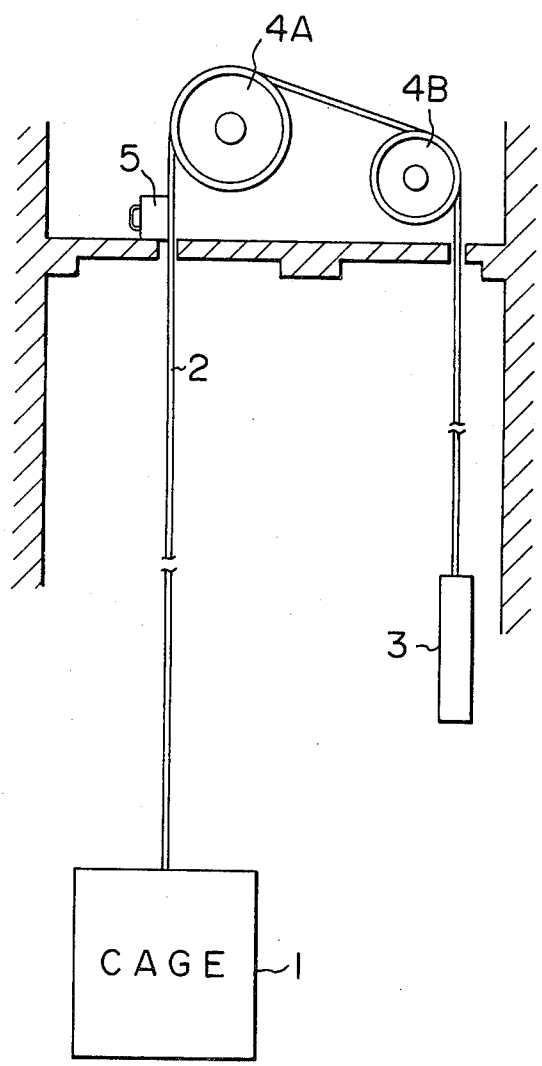
FIG. 1 is a schematic longitudinal sectional, side elevation view of an elevator system to which the present invention is applied.

An embodiment of the electromagnetic inspecting apparatus according to the present invention will now be described in detail with reference to FIGS. 1 to 4. This embodiment is specifically adapted to detect a defect present in a wire rope used for the traction of an elevator cage in an elevator system as shown in FIG. 1. Referring to FIG. 1, an elevator cage 1 is connected to one end of a wire rope 2 which is trained past a driver sheave 4A of steel and a follower sheave 4B of steel to be connected at the other end to a counterweight 3. The electromagnetic inspecting apparatus 5 embodying the present invention is disposed opposite to the wire rope 2 for detecting a defect which may be present in the wire rope 2.

Figure 2:
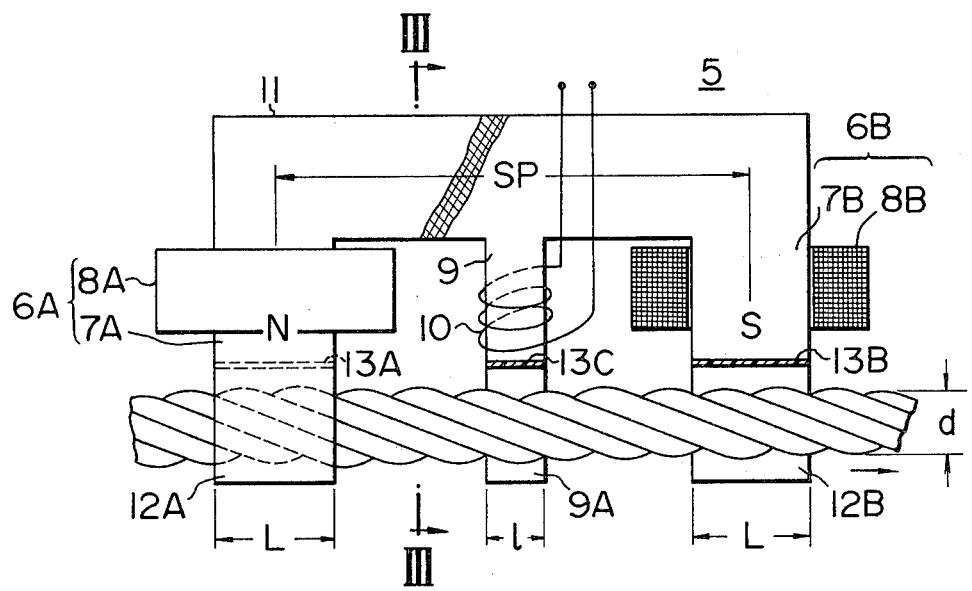
FIG. 2 is a partly cut-away, schematic side elevation view showing the basic structure of an embodiment of the electromagnetic inspecting apparatus according to the present invention.
Figure 3:
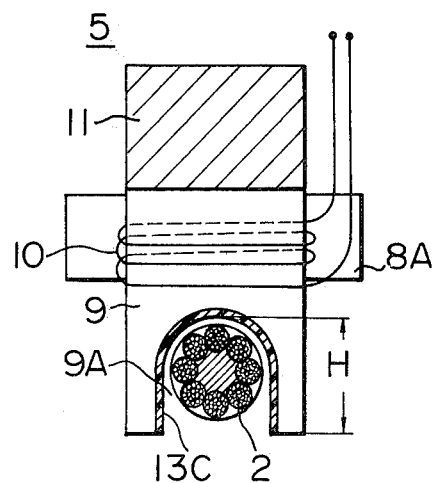
FIG. 3 is a schematic sectional view taken along the line III—III in FIG. 2.

FIG. 2 and FIG. 3 show the construction of the electromagnetic inspecting apparatus 5. Referring to FIGS. 2 and 3, a pair of magnetic poles 6A and 6B spaced apart by a predetermined distance from each other are disposed opposite to the wire rope 2 which is an elongate member of magnetic material, and a detecting core 9 is also disposed opposite to the wire rope 2 at a position intermediate the two magnetic poles 6A and 6B. These magnetic poles 6A and 6B have different polarities as shown in FIG. 1 and are composed of cores 7A, 7B and energizing coils 8A, 8B wound therearound respectively. A detecting coil 10 is wound around the detecting core 9 disposed between the magnetic poles 6A and 6B, and the ends of this detecting coil 10 are connected to a recorder (not shown), a display unit (not shown), an alarm unit (not shown) or the like. The magnetic poles 6A, 6B and the detecting core 9 are magnetically coupled together by a common yoke 11 at the portions remote from the wire rope 2. The energizing coils 8A and 8B are connected to a power source (not shown) through a switch (not shown).

The electromagnetic inspecting apparatus 5 has a basic structure as described above. The elongate member of magnetic material, which is the wire rope 2 herein, has a circular cross-sectional shape, and, therefore, limited portions of the magnetic poles 6A, 6B and detecting core 9 are only opposed by the wire rope 2, resulting in a very large magnetic reluctance. In order to ensure successful inspection, U-shaped grooves 12A, 12B and 9A for guiding the movement of the wire rope 2 in its longitudinal direction are formed in the associated areas of the magnetic poles 6A, 6B and detecting core 9 respectively in practical use. Coatings 13A, 13B and 13C of, for example, a wear resistive material are provided on the surface of the respective U-shaped guide grooves 12A, 12B and 9A so that the wire rope 2 may not make direct engagement with the magnetic poles 6A, 6B and detecting core 9. Such wear resistive coatings 13A, 13B and 13C are required to prevent accelerated wear of the cores 7A, 7B and 9 as a result of direct engagement of the wire rope 2 with the surface of the U-shaped grooves 12A, 12B and 9A formed in these cores. For the purpose above described, the surface of these U-shaped grooves 12A, 12B and 9A is finished to be sufficiently smooth. In the case of the coating 13C provided on the surface of the U-shaped groove 9A formed in the detecting core 9, an electrical insulating property is required in addition to the wear resisting property. This is because an electrical noise resulting in a lowered accuracy of defect detection appears in the detection output when the coating 13C is of a metal material and the wire rope 2 makes frictional engagement with the surface of such a metal coating. Suitable wear resistive materials include, for example, brass and phosphor bronze, and suitable wear resistive, electrical insulating materials include, for example, ceramics, tetrafluoroethylene, polyacetal resins, carbon and graphite. It is needless to mention that all of the coatings 13A to 13C may be provided by any one of such wear resistive, electrical insulating materials. In FIG. 2, the magnetic pole 6B, the detecting core 9, and a part of the yoke 11 are illustrated in a sectional view by being cut away by a plane parallel with the figure plane to show the state of the wire rope 2 received in the U-shaped grooves 12A, 9A and 12B. FIG. 3 shows the actual shape of the detecting core 9, and it is apparent that the remaining cores 7A and 7B have a shape similar to that shown in FIG. 3.

When the energizing coils 8A and 8B in the electromagnetic inspecting apparatus having such a structure are energized, and the wire rope 2 is moved in its longitudinal direction, for example, the direction shown by the arrow in FIG. 2, the detecting coil 10 detects a defect if it is present in the wire rope 2, so that the presence or absence of such a defect can be confirmed. For convenience of explanation, the energizing coils 8A and 8B are so energized that the magnetic pole 6A acts as an N-pole and the magnetic pole 6B acts as an S-pole, as shown in FIG. 2. When no defect is present in the wire rope 2, the magnetic flux flows through the route which is traced from the N-pole 6A-wire rope 2, S-pole, 6B-yoke 11 to the N-pole 6A. In this case, no voltage is induced in the detecting coil 10 since the magnetic flux does not flow through the detecting core 9.

Figure 4A:
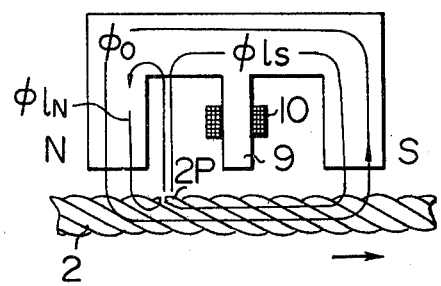
FIG. 4A and FIG. 4B illustrate how a defect present in an elongate member of magnetic material is detected by the electromagnetic inspecting apparatus of the present invention shown in FIG. 2.

The operation of the electromagnetic inspecting apparatus, when a defect is present in the wire rope 2, will be described with reference to FIGS. 4A and 4B. When a defect 2P present in the moving wire rope 2 is passing near the N-pole 6A but is still remote from the detecting core 9 as shown in FIG. 4A, a leakage flux $\phi_{lN}$ flowing through the N-pole 6A and the defect 2P in the wire rope 2 and another leakage flux $\phi_{ls}$ flowing through the S-pole 6B and the defect 2P in the wire rope 2 appear in addition to the main magnetic flux $\phi_o$ flow through the N-pole 6A, wire rope 2, S-pole 6B and yoke 11. However, no voltage is induced in the detecting coil 10 since the leakage fluxes do not substantially make interlinkage with the detecting coil 10.

Figure 4B:
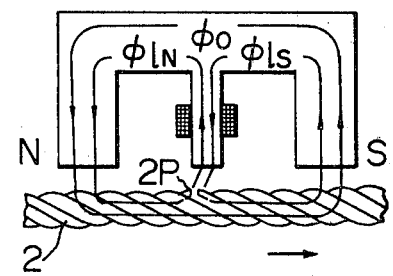

As the wire rope 2 continues to progressively move in the direction of the arrow until the defect 2P reaches the position directly opposite to the detecting core 9 disposed midway between the N-pole 6A and the S-pole 6B of the electromagnetic inspecting apparatus 5, the magnetic fluxes flow in a manner as shown in FIG. 4B. It will be seen in FIG. 4B that, although the flow of the main magnetic flux $\phi_o$ is the same as that shown in FIG. 4A, the leakage magnetic fluxes $\phi_{lN}$ and $\phi_{ls}$ flowing through the defect 2P pass through the detecting core 9 to make interlinkage with the detecting coil 10 and then return to the N-pole 6A and S-pole 6B respectively. However, when the defect 2P is passing the position exactly opposite to the center of the length 1 of the detecting core 9 when viewed in the moving direction of the wire rope 2, no voltage resulting from the appearance of the leakage fluxes $\phi_{lN}$ and $\phi_{ls}$ is induced in the detecting coil 10 since these two leakage fluxes $\phi_{lN}$ and $\phi_{ls}$ have the same flux density and flow in the directions opposite to each other.

Figure 5:
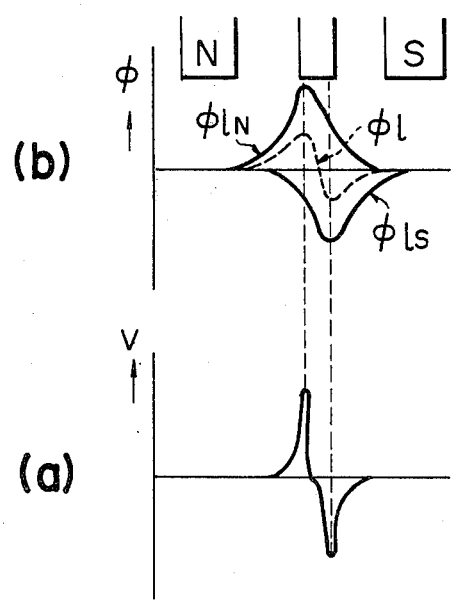
FIG. 5 illustrates the relation between the flows of leakage magnetic flux shown in FIGS. 4A and 4B and the output voltage generated from the electromagnetic inspecting apparatus of the present invention shown in FIG. 2.

However, before and after the defect 2P passes the position exactly opposite to the center of the length 1 of the detecting core 9, the flux densities of the two leakage fluxes $\phi_{lN}$ and $\phi_{ls}$ change with time as shown in FIG. 5(b). A leakage flux $\phi_l$ shown in FIG. 5(b) represents the difference between the flux densities of the leakage fluxes $\phi_{lN}$ and $\phi_{ls}$ making interlinkage with the detecting coil 10, and a voltage V proportional to the time-dependent change of the flux density of this composite leakage flux $\phi_l$, as shown in FIG. 5(a), is induced in the detecting coil 10. It is apparent that the higher the moving speed of the wire rope 2, the peak level of the induced voltage V is higher.

It will thus be seen that the electromagnetic inspecting apparatus according to the present invention is featured by the differential detection of two leakage fluxes flowing in directions opposite to each other. Although the detector disclosed in Japanese Utility Model Publication No. 2047/'75 cited hereinbefore is designed to similarly detect a leakage flux, it is adapted to merely detect a leakage flux flowing in one direction only. This point is the conspicuous difference between the prior art and the present invention.

Figure 6:
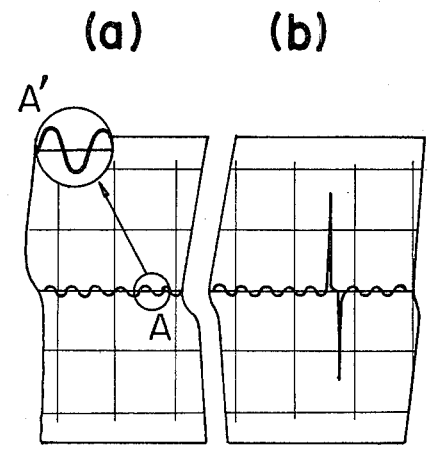
FIG. 6 illustrates voltage waveforms detected in FIGS. 4A and 4B and recorded on a recording sheet in a recorder.

The resultant output voltage signal from the detecting coil 10 is applied to a display unit such as an oscillograph (not shown) to be displayed thereon or is applied to an automatic recorder (not shown) to be recorded on a recording sheet. FIGS. 6(a) and 6(b) show the displayed or recorded waveform of the output signal from the detecting coil 10. FIG. 6(a) shows the waveform when the wire rope 2 is free from any defect, while FIG. 6(b) shows the waveform when the defect 2P present in the wire rope 2 passes the position opposite to the detecting core 9. It is preferable that the center-to-center distance SP of the magnetic poles 6A and 6B is selected to be N times (N: a positive integer) the strand pitch of the wire rope 2 as shown in FIG. 2. In such a case, a waveform analogous to a sinusoidal waveform appears as shown in an enlargement A' of a waveform portion A in FIG. 6(a) when the wire rope 2 is defect-free, so that the waveform can be easily distinguished from the waveform appearing when a defect 2P is present in the wire rope 2 and also from a noise waveform. On the other hand, when the defect 2P present in the wire rope 2 passes the position opposite to the detecting core 9, the output signal from the detecting coil 10 has a relatively low voltage level when the length l (FIG. 2) of the detecting core 9 in the longitudinal direction of the wire rope 2 is larger than the diameter d of the wire rope 2, while it shows a sharp impulse waveform as seen in FIG. 6(b) when the length l of the detecting core 9 is smaller than the diameter d of the wire rope 2.

The length L (FIG. 2) of each of the cores 7A and 7B of the respective magnetic poles 6A and 6B is selected to be a suitable value related to the diameter d of the wire rope 2 so that the wire rope 2 can be uniformly magnetized to provide a magnetic flux having a required flux density. Further, the depth H (FIG. 3) of each of the U-shaped grooves 12A, 12B and 9A is selected to be equal to or larger than the diameter d of the wire rope 2 so as to facilitate the detection of a defect throughout the entire periphery of the wire rope 2. Furthermore, due to the fact that the wear resistive, electrical insulating coatings 13A, 13B and 13C are provided to cover the surface of the U-shaped grooves 12A, 12B and 9A respectively, generation of noises resulting from frictional engagement of the wire rope 2 with the cores 7A, 7B and 9 can be positively prevented, and generation of knocking resulting from magnetic attraction of the wire rope 2 toward the cores 7A, 7B and 9 can also be positively prevented thereby ensuring smooth movement of the wire rope 2.

According to an experiment conducted by the inventors, it has been confirmed that the illustrated embodiment exhibits a very high sensitivity of defect detection and can detect, with sufficient accuracy, even a defect such as a cavity formed in an externally unseen portion of a wire or even a crinkle existing in an externally unseen portion of a wire, in addition to the detection of a break in an element wire of the wire rope 2.

Figure 7A:
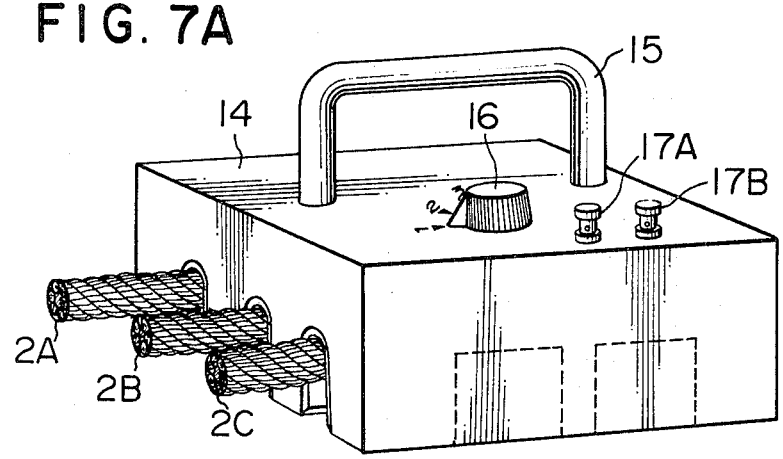
FIG. 7A is a schematic perspective view showing the external appearance of another embodiment of the electromagnetic inspecting apparatus of the present invention.
Figure 7B:
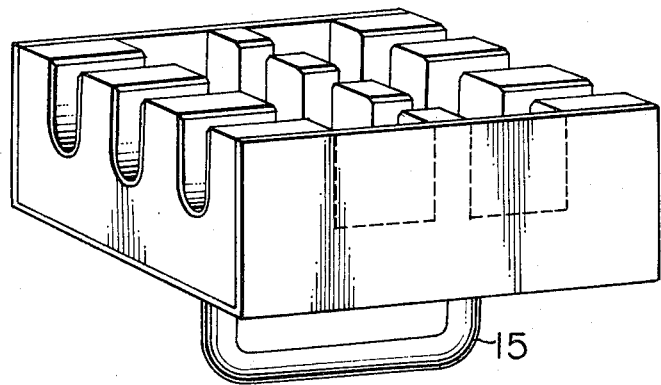
FIG. 7B is a schematic back view of FIG. 7A.

FIG. 7A shows a structure in which the electromagnetic inspecting apparatus 5 shown in FIGS. 2 and 3 is housed within a box-shaped casing 14 so as to facilitate handling of the apparatus 5, and a handle 15 is provided on the casing 14 so that the apparatus 5 can be carried to a desired site of inspection. In the structure shown in FIG. 7A, the magnetic poles and detecting core housed within the casing 14 are each formed with, for example, three spaced U-shaped grooves for independently receiving therein three juxtaposed wire ropes 2A, 2B and 2C respectively. A change-over switch 16 is provided so that the three wire ropes 2A to 2C can be selectively or sequentially inspected for detection of a defect. A recorder, a display unit, an alarm unit or the like (not shown) is connected as required to a pair of output terminals 17A and 17B of the detecting coil 10 shown in FIG. 2. Needless to mention, two or all of these three wire ropes 2A to 2C can be simultaneously inspected for detection of a defect. In such a case, it is necessary to provide two or three pairs of such output terminals. FIG. 7B is a schematic back view of FIG. 7A to show the arrangement of the U-shaped grooves.

The aforementioned embodiments of the electromagnetic inspecting apparatus can be conveniently used for the purpose of defect detection when wire ropes subject to inspection have the same diameter in individual elevator systems. However, when the wire ropes in the individual elevator systems have different diameters, a plurality of such electromagnetic inspecting apparatus having U-shaped grooves of respectively different sizes must be prepared to deal with the different rope diameters. Also, when a plurality of wire ropes are to be simultaneously subjected to inspection, a plurality of such electromagnetic inspecting apparatus corresponding to the number of the wire ropes must be prepared.

Figure 8:
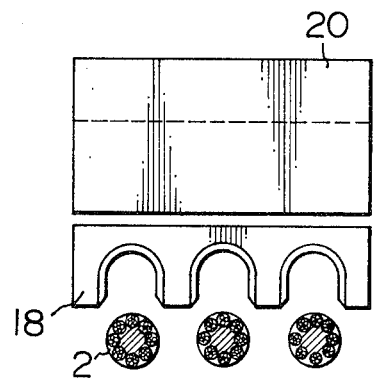
FIG. 8 and FIG. 9 are schematic front elevation views of modifications of further embodiments of the electromagnetic inspecting apparatus of the present invention, comprising a grooved part detachably coupled to a principal functional part.
Figure 9:
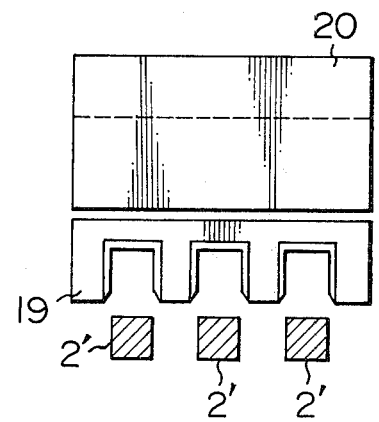

FIG. 8 and FIG. 9 show a further embodiment of the present invention which obviate such an inconvenience and wherein a plurality of different grooved parts respectively formed with a plurality of U-shaped grooves satisfying various conditions of elongate magnetic material subject to inspection (such as, the external shape, the dimensions, etc. of the elongate magnetic member) are separately provided so that a desired one of the grooved parts may be detachably coupled to a commonly prepared principal functional part of the detector. Referring to FIG. 8, a grooved part 18 for three wire ropes is detachably coupled to the common principal functional part 20, while in FIG. 9 a grooved part 19 for three elongated square bars is detachably coupled to the common principal functional part 20 of the detector. This common principal functional part 20 includes, for each elongate magnetic member, a portion of the cores 7A and 7B of the respective magnetic poles 6A and 6B, the energizing coils 8A and 8B, a portion of the detecting core 9, the detecting coil 10 and the yoke 11 shown in FIG. 2. On the other hand, each of the grooved parts 18 and 19 includes, for each elongate magnetic member the remaining portions of the cores 7A, 7B and 9. The core arrangement must be such that the portions of the cores 7A, 7B and 9 in the principal functional part 20 register with the remaining portions thereof in the grooved part 18 or 19 respectively when the grooved part 18 or 19 is coupled to the principal functional part 20.

The cores 7A, 7B, 9 and the yoke 11 described above are separately prepared, and the cores are joined or coupled together by the yoke. However, the cores and the yoke may be integrally made in the form of a generally E shaped core so as to reduce the number of manufacturing steps and also to reduce the internal magnetic reluctance because of the absence of any joints.

In the aforementioned embodiments, the magnetic poles 6A and 6B are each composed of a core and an energizing coil. However, these magnetic poles 6A and 6B may be replaced by blocks of permanent magnet material. Also, each of the magnetic poles 6A, 6B and yoke 11 may be in the form of a block of permanent magnet material. Further, the yoke 11 and magnetic poles 6A, 6B of permanent magnet material may be integrally formed in a generally U-shaped permanent magnet. Furthermore, only the yoke 11 may be in the form of a block of permanent magnet material, and the magnetic poles 6A and 6B may be in the form of blocks of soft iron respectively. All of such embodiments are also included in the scope of the present invention. Moreover, it is unnecessary to provide the coatings 13A, 13B and 13C in the U-shaped grooves 12A, 12B and 9A when the cores 7A and 7B of the magnetic poles 6A, 6B and the detecting core 9 are made of a wear resistive, electrical insulating material, for example, ferrite which is a permanent magnet material and also an electrical insulator.

Figure 10:
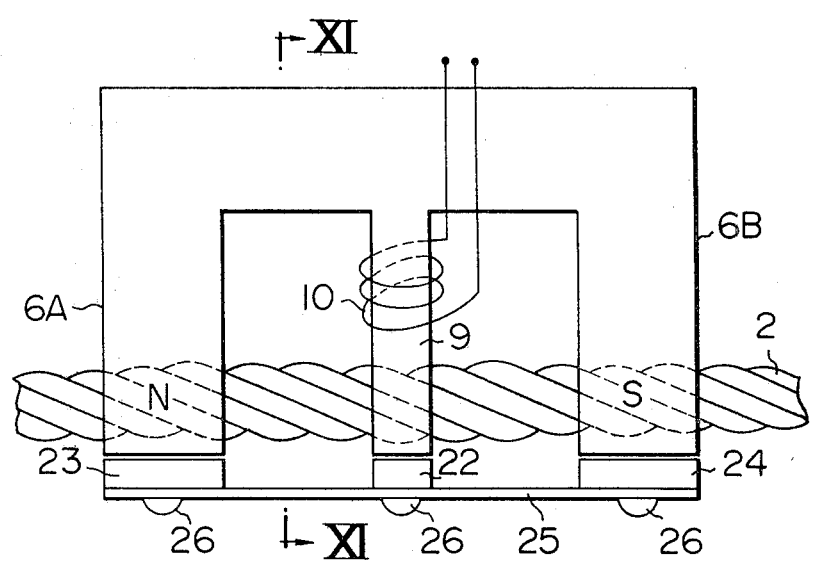
FIG. 10 is a schematic side elevation view of another embodiment of the electromagnetic inspecting apparatus according to the present invention.
Figure 11:
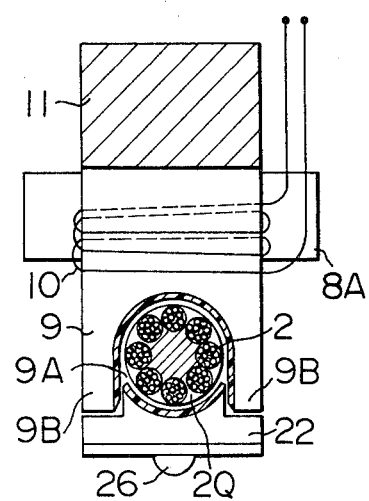
FIG. 11 is a schematic sectional view taken along the line XI—XI in FIG. 10.

In another embodiment or a modification of the present invention as shown in FIGS. 10 and 11, a cover member 22 of magnetic material is detachably mounted to bridge the legs 9B, 9B defining therebetween the U-shaped groove 9A of the detecting core 9 so as to improve the sensitivity of detection of a defect 2Q which may be present in a portion of the wire rope 2 appearing at the opening of the U-shaped groove 9A. The inner surface of this cover member 22 is preferably shaped to be arcuately concaved to conform to the external contour of the wire rope 2, and a coating similar to the coating 13C provided in the U-shaped groove 9A of the detecting core 9 is also provided on the inner surface of the cover member 22. This cover member 22 may be detachably mounted on the detecting core 9 by means such as bolts. However, this manner of detachably mounting the cover member 22 on the detecting core 9 is not so easy as a matter of fact. It is therefore preferable to mount independent cover members 23 and 24 similar to the cover member 22 on the magnetic poles 6A and 6B so as to bridge the legs defining the U-shaped grooves 12A and 12B of the cores 7A and 7B respectively, as shown in FIG. 10. Then, when these cover members 22, 23 and 24 are detachably fixed as by bolts 26 to a connecting member 25 made of a suitable flexible material such as a flexible synthetic resin material, the cover members 23 and 24 are attracted toward and onto the respective magnetic poles 6A and 6B so that the cover member 22 can be maintained in its position tightly covering the U-shaped groove 9A of the detecting core 9. To this end, the connecting member 25 must be so shaped that, when the cover members 23 and 24 are attracted toward and onto the respective magnetic poles 6A and 6B, the cover member 22 is pressed against the detecting core 9 with a force which is enough to prevent formation of a gap between the cover member 22 and the associated ends of the legs 9B, 9B defining the U-shaped groove 9A. For this purpose, suitable flexibility is required for the connecting member 25.

Needless to mention, such cover members are also preferably provided in the embodiments shown in FIGS. 7 to 9.

Although the aforementioned embodiments have been described to illustrate an application of the present invention to the detection of a defect present in a wire rope by way of example, it is apparent that the present invention is equally effectively applicable to the detection of a defect present in a member of magnetic material in the form of wire, in the form of bar or in the form of plate. While it is necessary to provide a groove in each of the cores in such a case, the shape of the grooves is naturally suitably selected depending on the external shape of a member for which the presence or absence of a defect is to be detected. These embodiments are naturally also included in the scope of the present invention.

We claim:

1. An electromagnetic inspecting apparatus for electromagnetically detecting a defect present in a magnetizable wire rope, said wire rope having a plurality of strands, each of said strands including a plurality of steel wires comprising:

a first magnetic pole disposed opposite to said magnetizable wire rope which moves in its longitudinal direction;

a second magnetic pole having a polarity different from that of said first magnetic pole and disposed opposite to said magnetizable wire rope at a position spaced apart by a predetermined distance from said first magnetic pole in said longitudinal direction, said predetermined distance being selected to be a multiple integer of the strand pitch of said magnetizable wire rope;

a detecting core disposed opposite to said magnetizable wire rope at a position intermediate said first and second magnetic poles;

a detecting coil wound around said detecting core to make a differential response to flows of leakage flux appearing due to the presence of a defect in said magnetizable wire rope thereby generating an electrical output signal indicative of the result of its response; and a yoke magnetically coupling said first and second magnetic poles and said detecting core at the portions remote from said magnetizable wire rope.

2. An electromagnetic inspecting apparatus as claimed in claim 1, wherein said magnetizable wire rope is for use in an elevator system.

3. An electromagnetic inspecting apparatus as claimed in claim 1, wherein a guide groove for guiding the movement of said magnetizable wire rope in said longitudinal direction is formed in each of said first and second magnetic poles and said detecting core at the surface opposite to said magnetizable wire rope.

4. An electromagnetic inspecting apparatus as claimed in claim 3, wherein said magnetizable wire rope is for use in an elevator system.

5. An electromagnetic inspecting apparatus as claimed in claim 3 wherein each of said guide grooves is generally U-shaped.

6. An electromagnetic inspecting apparatus as claimed in claim 5, wherein the depth of each of said U-shaped grooves is selected not to be smaller than the diameter of said wire rope.

7. An electromagnetic inspecting apparatus as claimed in claim 5, wherein at least said U-shaped groove formed in said detecting core, among said U-shaped grooves, is provided with a coating of electrical insulating material at the surface opposite to said magnetizable wire rope.

8. An electromagnetic inspecting apparatus as claimed in claim 5, wherein each of said U-shaped grooves formed in said first and second magnetic poles is provided with a coating of material, which is at least wear resistive, at the surface opposite to said magnetizable wire rope, and said U-shaped groove formed in said detecting core is provided with a coating of electrical insulating material at the surface opposite to said magnetizable wire rope.

9. An electromagnetic inspecting apparatus as claimed in claim 7 or 8, wherein at least said U-shaped groove formed in said detecting core, among said U-shaped grooves, is covered with a detachable cover member of magnetic material which acts to magnetically bridge the legs defining therebetween said U-shaped groove of said detecting core.

10. An electromagnetic inspecting apparatus as claimed in claim 7 or 8, wherein said U-shaped grooves formed in said first and second magnetic poles and said detecting core are covered with independent detachable members of magnetic material which act to magnetically bridge the legs defining therebetween said U-shaped grooves of said first and second magnetic poles and said detecting core respectively, and said cover members are integrally connected together by a connecting member so that, when said detachable cover members covering said U-shaped grooves of said first and second magnetic poles are magnetically attracted toward and onto the associated ends of the legs defining therebetween said U-shaped grooves, said detachable cover member covering said U-shaped groove of said detecting core can be pressed against the associated ends of the legs defining therebetween said U-shaped groove of said detecting core.

11. An electromagnetic inspecting apparatus as claimed in claim 10, wherein the inner surface of each of said cover members is shaped to be arcuately concaved to conform to the external contour of said wire rope and is provided with a coating of electrical insulating material.

12. An electromagnetic inspecting apparatus as claimed in claim 10 wherein, the inner surface of at least said cover member covering said U-shaped groove of said detecting core, among said cover members, is shaped to be accurately concaved to conform to the external contour of said wire rope and is provided with a coating of electrical insulating material.

13. An electromagnetic inspecting apparatus as claimed in claim 10, wherein the inner surface of said cover member covering said U-shaped groove of said detecting core, among said cover members, is provided with a coating of electrical insulating material, and the inner surface of each of said cover members covering said U-shaped grooves of said first and second magnetic poles is provided with a coating of material which is at least wear resistive.

14. An electromagnetic inspecting apparatus as claimed in claim 1, 3, 5, 6, 7, 8 or 2, wherein said first and second magnetic poles are each formed by a core and an electromagnetic coil wound around said core to constitute an electromagnet.

15. An electromagnetic inspecting apparatus as claimed in claim 14, wherein the cores of said first and second magnetic poles, said detecting core and said yoke are integrally made in the form of a generally E-shaped core.

16. An electromagnetic inspecting apparatus as claimed in claim 1, 3, 5, 6, 7, 8 or 2, wherein said first and second magnetic poles are each in the form of a block of permanent magnet.

17. An electromagnetic inspecting apparatus as claimed in claim 16, wherein said yoke is in the form of a block of permanent magnet.

18. An electromagnetic inspecting apparatus as claimed in claim 1, 3, 5, 6, 7, 8 or 2, wherein said yoke is in the form of a block of permanent magnet, and said first and second magnetic poles are in the form of blocks of soft iron mounted on the respective poles of said block of permanent magnet.

19. An electromagnetic inspecting apparatus as claimed in claim 1, 3, 5, 6, 7, 8 or 2, wherein said first and second magnetic poles and said yoke are integrally made in the form a generally U-shaped permanent magnet.

20. An electromagnetic inspecting apparatus as claimed in claim 1, 3, 5, 6, 7, 8 or 2, wherein said apparatus is housed within a portable casing so that said apparatus can achieve defect inspection in the state housed within said casing.

21. An electromagnetic inspecting apparatus as claimed in claim 20, wherein said casing includes a first section and a second section, and each of said first and second magnetic poles and said detecting core includes a first portion including the ends of the groove-defining legs located opposite to said magnetizable wire rope and a second portion other than said first portion, said first section of said casing housing therein the first portions of said first and second magnetic poles and said detecting core to constitute a first assembly providing a grooved part of the detector, said second section of said casing housing therein the second portions of said first and second magnetic poles and said detecting core to constitute a second assembly providing a principal function part of the detector, and said first and second assemblies being detachably coupled together to establish the integral combination of said first and second magnetic poles and said detecting core, so that, from among a plurality of first assemblies analogous to said first assembly but having different-sized grooved portions depending on a plurality of different diameter wire rope to be inspected, the one most suitable for a magnetizable wire rope to be inspected can be selected in use and can then be coupled to said first assembly to complete said apparatus.

22. An electromagnetic inspecting apparatus for electromagnetically detecting a defect present in a plurality of magnetizable wire ropes, each of said wire ropes having a plurality of strands, each of said strands including a plurality of steel wires, each of said wire ropes moveing in parallel with each other in their longitudinal direction, and including a plurality of electromagnetic inspecting units provided for the inspection of said plural magnetizable wire ropes respectively, each of said units comprising:
a first magnetic pole disposed opposite to an associated one of said magnetizable wire ropes;
a second magnetic pole having a polarity different from that of said first magnetic pole and disposed opposite to said associated magnetizable wire rope at a position spaced apart by a predetermined distance from said first magnetic pole in said longitudinal direction, said predetermined distance being selected to be a multiple integer of the strand pitch of said magnetizable wire rope;
a detecting core disposed opposite to said associated magnetizable wire rope at a position intermediate said first and second magnetic poles;
a detecting coil wound around said detecting core to make a differential response to flows of leakage flux appearing due to the presence of a defect in said associated magnetizable wire rope thereby generating an electrical output signal indicative of the result of its response; and
a yoke magnetically coupling said first and second magnetic poles and said detecting core at the portions remote from said associated magnetizable wire rope.

23. An electromagnetic inspecting apparatus as claimed in claim 22, wherein said plurality of magnetizable wire ropes are for use in an elevator system.

24. An electromagnetic inspecting apparatus as claimed in claim 22, wherein, in each of said units, a guide groove for guiding the movement of said associated magnetizable wire rope in said longitudinal direction is formed in each of said first and second magnetic poles and said detecting core at the surface opposite to said associated magnetizable wire rope.

25. An electromagnetic inspecting apparatus as claimed in claim 24, wherein said plurality of magnetizable wire ropes are for use in an elevator system.

26. An electromagnetic inspecting apparatus as claimed in claim 24 wherein each of said guide grooves is generally U-shaped.

27. An electromagnetic inspecting apparatus as claimed in claim 26 wherein the depth of each of said U-shaped grooves is selected not to be smaller than the diameter of said wire rope.

28. An electromagnetic inspecting apparatus as claimed in claim 26, wherein, in each of said units, at least said U-shaped groove formed in said detecting core, among said U-shaped grooves, is provided with a coating of electrical insulating material at the surface opposite to said associated magnetizable wire rope.

29. An electromagnetic inspecting apparatus as claimed in claim 26, wherein, in each of said units, each of said U-shaped grooves formed in said first and second magnetic poles is provided with a coating of material, which is at least wear resistive, at the surface opposite to said associated magnetizable wire rope, and said U-shaped groove formed in said detecting core is provided with a coating of electrical insulating material at the surface opposite to said associated magnetizable wire rope.

30. An electromagnetic inspecting apparatus as claimed in claim 28 or 29, wherein, in each of said units, at least said U-shaped groove formed in said detecting core, among said U-shaped grooves, is covered with a detachable cover member of magnetic material which acts to magnetically bridge the legs defining therebetween said U-shaped groove of said detecting core.

31. An electromagnetic inspecting apparatus as claimed in claim 28 or 29, wherein, in each of said units, said U-shaped grooves formed in said first and second magnetic poles and said detecting core are covered with independent detachable cover members of magnetic material which act to magnetically bridge the legs defining therebetween said U-shaped grooves of said first and second magnetic poles and said detecting core respectively, and said cover members are integrally connected together by a connecting member so that, when said detachable cover members covering said U-shaped grooves of said first and second magnetic poles are magnetically attracted toward and onto the associated ends of the legs defining therebetween said U-shaped grooves, said detachable cover member covering said U-shaped groove of said detecting core can be pressed against the associated ends of the legs defining therebetween said U-shaped groove of said detecting core.

32. An electromagnetic inspecting apparatus as claimed in claim 31, wherein the inner surface of each of said cover members is shaped to be arcuately concaved to conform to the external contour of said wire rope and is provided with a coating of electrical insulating material.

33. An electromagnetic inspecting apparatus as claimed in claim 32, wherein the inner surface of at least said cover member covering said U-shaped groove of said detecting core, among said cover members, is shaped to be arcuately concaved to conform to the external contour of said wire rope and is provided with the coating of electrical insulating material.

34. An electromagnetic inspecting apparatus as claimed in claim 31, wherein the inner surface of said cover member covering said U-shaped groove of said detecting core, among said cover members, is provided with a coating of electrical insulating material, and the inner surface of each of said cover members covering said U-shaped grooves of said first and second magnetic poles is provided with a coating of material which is at least wear resistive.

35. An electromagnetic inspecting apparatus as claimed in claim 22, 24, 26, 27, or 23, wherein, in each of said units, said first and second magnetic poles are each formed by a core and an electromagnetic coil wound around said core to constitute an electromagnet.

36. An electromagnetic inspecting apparatus as claimed in claim 31, wherein, in each of said units, the cores of said first and second magnetic poles, said detecting core and said yoke are integrally made in the form of a generally E-shaped core.

37. An electromagnetic inspecting apparatus as claimed in claim 22, 24, 26, 27, or 23, wherein, in each of said units, said first and second magnetic poles are each in the form of a block of permanent magnet.

38. An electromagnetic inspecting apparatus as claimed in claim 37, wherein, in each of said units, said yoke is in the form of a block of permanent magnet.

39. An electromagnetic inspecting apparatus as claimed in claim 22, 24, 26, 27, or 23, wherein, in each of said units, said yoke is in the form of a block of permanent magnet, and said first and second magnetic poles are in the form of blocks of soft iron mounted on the respective poles of said block of permanent magnet.

40. An electromagnetic inspecting apparatus as claimed in claim 22, 24, 26, 27, or 23, wherein, in each of said units, said first and second magnetic poles and said yoke are integrally made in the form of a generally U-shaped permanent magnet.

41. An electromagnetic inspecting apparatus as claimed in claim 22, 24, 26, 27, or 23, wherein said apparatus is housed within a portable casing so that said apparatus can achieve defect inspection in the state housed within said casing.

42. An electromagnetic inspecting apparatus as claimed in claim 41, wherein said casing includes a first section and a second section, and, in each of said units, each of said first and second magnetic poles and said detecting core includes a first portion including the ends of the groove-defining legs located opposite to said associated magnetizable wire ropes and a second portion other than said first portion, said first section of said casing housing therein the first portions of said first and second magnetic poles and said detecting core to constitute a first assembly providing a grooved part of the detector, said second section of said casing housing therein the second portions of said first and second magnetic poles and said detecting core to constitute a second assembly providing a principal functional part of the detector, and said first and second assemblies being detachably coupled together to establish the integral combination of said first and second magnetic poles and said detecting core in each of said units, so that, from among a plurality of first assemblies analogous to said first assembly but having different-sized grooved portions depending on a plurality of different diameter magnetizable wire ropes to be inspected, the one most suitable for the inspection of magnetizable wire ropes to be inspected can be selected in use and can then be coupled to said second assembly to complete said apparatus.

* * * * *